US00PP09910P

United States Patent [19]

Bergman

[11] Patent Number: Plant 9,910

[45] Date of Patent: Jun. 3, 1997

[54] AZALEA PLANT 'CHERISH'

[75] Inventor: Wendy R. Bergman, Lehigh Acres, Fla.

[73] Assignee: Yoder Brothers, Inc., Barberton, Ohio

[21] Appl. No.: 583,478

[22] Filed: Jan. 5, 1996

[51] Int. Cl.[6] ..... A01H 5/00

[52] U.S. Cl. ..... Plt./56

[58] Field of Search ..... Plt./55, 56, 57

*Primary Examiner*—James R. Feyrer

*Attorney, Agent, or Firm*—Foley & Lardner

[57] ABSTRACT

An azalea plant named Cherish, particularly characterized by its evergreen foliage, semi-double hose-in-hose flower form with slightly frilled margins, coral-pink flower color with a dark coral-pink blotch, ease of budding, uniform and dense plant habit, free branching, rapid and uniform flower response in a year round controlled program, excellent cooler tolerance and very good keeping quality.

1 Drawing Sheet

The present invention comprises a new and distinct cultivar of Azelea, a greenhouse forcing type, hereinafter referred to as Cherish.

Cherish, identified as Code 1037 during the selection process, originated from a planned cross hybridization between two selected breeding lines in a controlled breeding program in Fort Myers, Fla.

The female, or seed parent of Cherish is the unpatented cultivar Alaska, a white single to semi-double. The male, or pollen parent is a seedling known as Code 227, a proprietary breeding line.

Cherish was discovered and selected by Wendy R. Bergman as one flowering plant within the progeny of the stated cross in January 1992, in Fort Myers, Fla.

The first asexual reproduction of Cherish was accomplished when vegetative cuttings were taken from the initial selection in April 1992, in Fort Myers, Fla., by technicians working under formulations established and supervised by Wendy R. Bergman.

Horticultural examination of controlled flowerings of successive generations of plants derived from cuttings taken from the original selection has shown that the unique combination of characteristics as herein disclosed for Cherish are fixed and retained through successive generations of asexual reproduction.

Cherish has not been observed under all possible environmental conditions. The phenotype may vary signficantly with variations in environment such as temperature, light intensity and day length, without, however, any variance in the genotype.

The following observations, measurements and comparisons describe plants that were grown in Fort Myers, Fla. in a controlled greenhouse environment and following a commercial schedule.

The following traits have been repeatedly observed and are determined to be basic characteristics of Cherish, which, in combination, distinguish this azalea as a new and distinct cultivar:

1. Coral-pink flower color (48C) with a dark coral-pink blotch.
2. Semi-double hose-in-hose flower form with a slightly ruffled petal margin.
3. The flowers range in size from 7.5 to 10.0 cm in diameter with 9.5 cm the avarage size.
4. Spreading, dense and symmetrical plant habit.
5. Fast, uniform response in year round controlled flowering programs, forcing in 30 days on average.
6. Good longevity in a simulated home environment, with flowers lasting up to 25 days.
7. Excellent foliage retention and no flower bud damage when cooled for 6 weeks with no lighting at 38° F.

The accompanying color photograph shows in perspective view the unique features of the new cultivar, with colors being as true as possible with color illustrations of this type.

Of the commercial cultivars known to the inventor, the most similar in comparison to Cherish is the unpatented cultivar Gloria. Cherish is similar to Gloria in having coral-pink flower color, but the colors of the respective cultivar are not precisely the same. Both Cherish and Gloria have similar spreading, dense, compact plant habits, and dark green glossy foliage.

Cherish differs from Gloria in that Cherish has larger, more fully petaled flowers and does not posess a white petal margin.

In the following description color references are made to The Royal Horticultural Society Colour Chart. The color values were determined on Mar. 13, 1995. All readings were taken in an office under cool white fluorescent lights, facing a west window between the hours of 10:00 a.m and 2:00 p.m.

Classification:

*Botanical* .—*Rhododendron hybrida*, evergreen type.

*Commercial*.—Florist forcing pot azalea, cv. Cherish.

Inflorescence

Flower (general):

*Size*.—7.5 to 10.0 cm.

*Born*.—Terminal cluster, usually three (3) per bud, ranging from two to four (2–4). Occasionally more than one bud per stem.

*Form*.—Hose-in-hose. Funnel-form.

*Blooming habit*.—Once profusely. Buds easily and uniformly in a year-round flowering program. The majority of terminal buds break color within one (1) week of the first. Flowering begins approximately 30 days after the start of forcing.

*Fragrance*.—Slight.

Corolla (petals):

*Texture*.—Soft.

*Substance*.—Heavy.

*Shape*.—Rounded with slightly undulate margin.

*Color (fully open)*.—Generally 48C, coral-pink. Upper Surface: Edge: 48C. Center: 48C. Base: 48D. Lower surface: 43D. Blotch: 48A.

Bud:

*Size*.—Medium.

*Shape*.—Conoidal.

*Color*.—Mixture of 48A, 48B, and 48C.

*Bud sheath.*—Light green with light brown hairs.

Calyx:

*Form.*—Petaloid (hose-in-hose). Irregularly lobed margin.

*Color.*—48C. Lower surface: 43D.

Peduncle:

*Length.*—1.3–2.5 cm.

*Strength.*—Strong.

*Aspect.*—Pubescent.

Reproductive organs:

*Androecium* (*stamens*).—Number: Zero to five (0–5), many are petaloid. Anthers: 185A. Filaments: Length: 1.6–2.8 cm. Color: 49B.

*Gynoecium* (*pistil*).—Stigma: 145A. Style: Length: 0.3–3.7 cm. Color: 51B. Ovary: Pubescent.

Plant characteristics:

Foliage:

*Type.*—Evergreen.

*Arangement.*—Alternate.

*Shape.*—Obovate.

*Size.*—Length: 2.0–6.5 cm. Width: 1.3–3.0 cm.

*Margin.*—Entire.

*Color.*—Immature: Upper surface: 143A. Lower Surface: 144A. Mature: Upper surface: Between 136A. and 147A. Lower surface: 147B.

*Texture.*—Leathery.

*Tomentum.*—Present on upper surface. Insignificant.

Stems:

*Color.*—Immature: 145A. Mature: Between 165A and 165B. Tomentum: Present, dark brown, Insignificant.

Plant habit: Compact, spreading, dense bush which is uniform and symmetrical in a six-inch (6") pot when pinched three (3) times. Total crop time to the dormant budded stage is 40–42 weeks to produce a plant approximately 35 cm in diameter and having a total height of 30–36 cm. Internode lengths may vary widely from 2–28 mm on the same stem.

Branching habit: Free branching, three to five (3–5) breaks a vegetative cutting is pinched.

Rooting: Roots easily in eight to ten (8–10) weeks with 75° F. soil temperature.

Budding ease: Plants produce flower buds easily and uniformly year round with the use of commercially available plant growth regulators. Natural season response has not been ascertained.

Cooler tolerance: Plants placed in a cooler as a means of breaking dormancy perform very well. Cherish is tolerant of six (6) weeks in an unlighted cooler at 38F. without any bud damage or foliage loss occuring.

Blooming: Plants reach the stage of 12 buds showing color in 30 days on average after the cooling treatment. This varies from 24 to 38 days depending upon time of year. Cherish flowers uniformly and profusely across the plant.

Shelf life: When plants are moved to an office or home environment at the stage of eight (8) open flowers, they maintain an attractive appearance for 25 days on average.

It is claimed:

1. A new and distinct cultivar of azalea named Cherish, as described and illustrated.

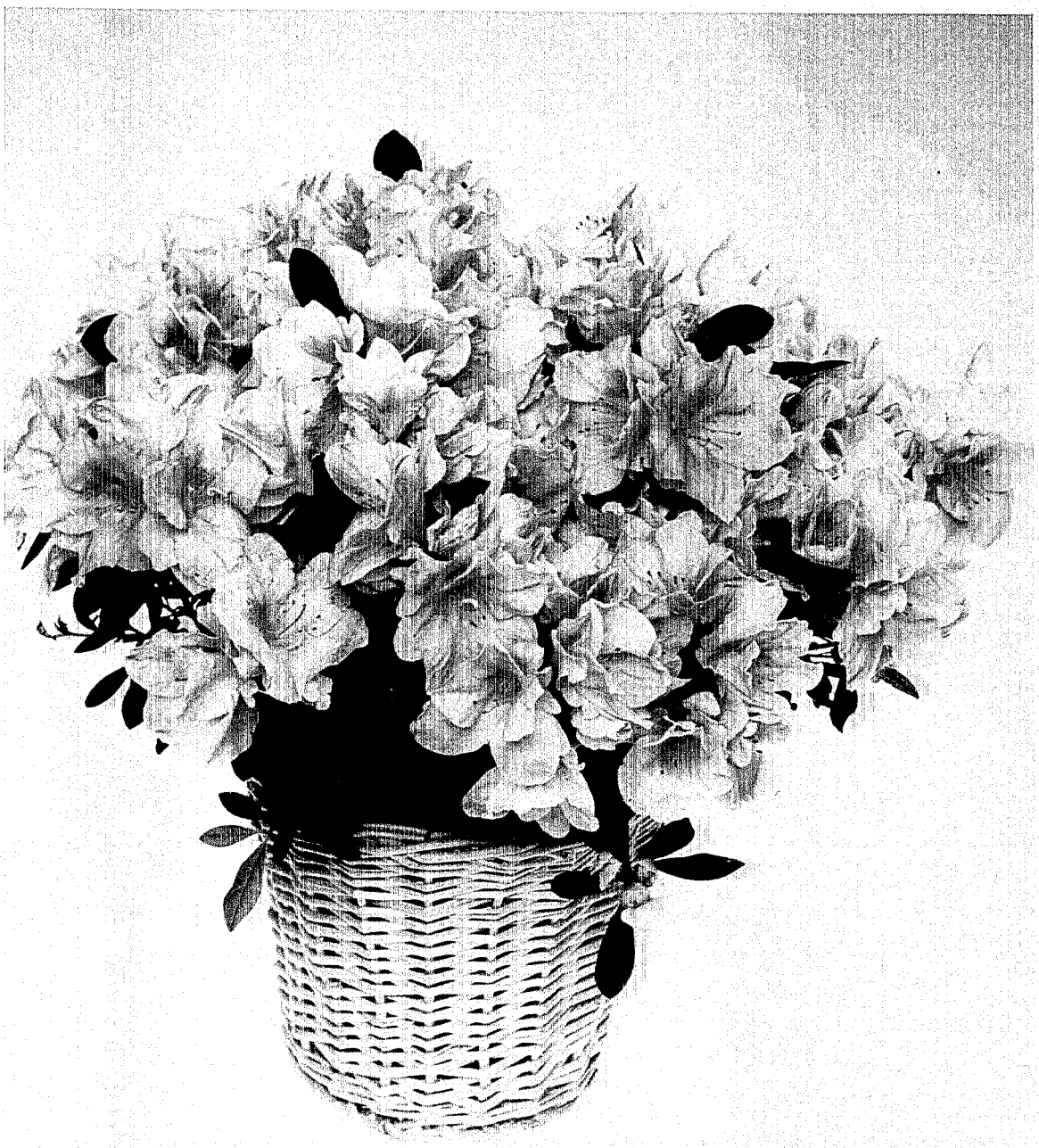

* * * * *